United States Patent
Cao et al.

(10) Patent No.: US 10,882,818 B1
(45) Date of Patent: Jan. 5, 2021

(54) P-BROMOANILINE CASSIC ACID ESTER WITH ANTIBACTERIAL ACTIVITY AND A METHOD OF PREPARING THE SAME

(71) Applicants: Wenqiang Cao, Zhuhai (CN); Hong Liu, Zhuhai (CN); Chengyuan Liang, Zhuhai (CN); Yikang Chen, Zhuhai (CN); Haiwei Li, Zhuhai (CN); Kangxiong Wu, Zhuhai (CN)

(72) Inventors: Wenqiang Cao, Zhuhai (CN); Hong Liu, Zhuhai (CN); Chengyuan Liang, Zhuhai (CN); Yikang Chen, Zhuhai (CN); Haiwei Li, Zhuhai (CN); Kangxiong Wu, Zhuhai (CN)

(73) Assignee: ZHUHAI JINAN SELENIUM SOURCE NANOTECHNOLOGY CO., LTD., Zhuhai (CN)

( * ) Notice: Subject to any disclaimer, the term of this patent is extended or adjusted under 35 U.S.C. 154(b) by 0 days.

(21) Appl. No.: 16/932,430

(22) Filed: Jul. 17, 2020

(51) Int. Cl.
*C07C 233/65* (2006.01)
*C07C 231/02* (2006.01)
*C07C 231/24* (2006.01)

(52) U.S. Cl.
CPC .......... *C07C 233/65* (2013.01); *C07C 231/02* (2013.01); *C07C 231/24* (2013.01)

(58) Field of Classification Search
CPC ... C07C 233/00; C07C 231/02; C07C 231/24; C07C 233/65
See application file for complete search history.

(56) References Cited

U.S. PATENT DOCUMENTS 10,717,699 B1 * 7/2020 Luo .................... C07C 67/08

\* cited by examiner

*Primary Examiner* — Jafar F Parsa

(57) ABSTRACT

A compound having the formula (I):

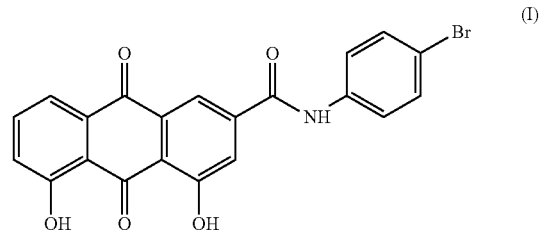

is disclosed. A method of preparing the compound of formula (I) is also disclosed.

15 Claims, 2 Drawing Sheets

P-BROMOANILINE CASSIC ACID ESTER WITH ANTIBACTERIAL ACTIVITY AND A METHOD OF PREPARING THE SAME

FIELD OF THE INVENTION

The present invention relates to the field of medicinal chemistry, and in particular, to a p-bromoaniline cassic acid ester with anti-resistant bacteria activity and a method of preparing the same.

BACKGROUND OF THE INVENTION

The existing antibacterial drugs include β-lactams, aminoglycosides, macrolides, chloramphenicol, fluoroquinolones, folic acid pathway inhibitors, glycopeptides and tetracyclines. Over the years, various types of drug-resistant bacteria have developed rapidly, and the abuse of antibiotics is the main reason for the emergence of drug-resistant bacteria. For example, P. aeruginosa can change the permeability of the cell membrane and prevent the entry of penicillin drugs; Mycobacterium tuberculosis prevents the binding of antibiotics by changing the protein structure in the body; What's more, some Gram-negative bacteria can take the initiative to attack and hydrolyze penicillin and cephalosporin drugs. Bacteria can not only pass the mutated gene to the next generation, but also pass the drug resistance to the heterologous strain through direct contact, plasmid transmission, etc., which makes medical scientists a headache. Today, the problem of drug-resistant bacteria in China has become very prominent. The number of nosocomial infections caused by drug-resistant bacteria has accounted for about 30% of the total number of infectious patients in hospitals. Solving the problem of drug resistance has become a top priority.

Cassic acid (also known as rhein) is a natural anthraquinone compound (compound of formula II), which has a variety of biological and pharmacological activities and can be extracted from rhubarb. It has many effects, such as improving glucose and lipid metabolism, protecting liver, anti-fibrosis, anti-oxidation, anti-inflammation, antibacterial, anti-cancer and anti-tumor. However, its clinical application is limited to a great extent because of its poor water solubility and low bioavailability.

P-bromoaniline is a chemical intermediate (compound of formula III) widely used in the synthesis of fine chemical products, such as medicine, dyes and pigments. It can be used as an intermediate of anti-cancer drugs and coumarin fluorescent dyes.

In the present invention, cassic acid is modified by the p-bromoaniline structure to obtain a p-bromoaniline cassic acid ester. Preliminary antibacterial activity experiment shows that the compound has excellent antibacterial activity and has high medical research and application value in the treatment of infectious diseases caused by multidrug resistant bacteria.

SUMMARY OF THE INVENTION

In one embodiment, the present invention provides a p-bromoaniline cassic acid ester, which can be used as a new type of antibacterial drug for treating infectious diseases caused by multi-drug resistant bacteria infection. The structural formula of the compound of the present invention is as shown in Formula I:

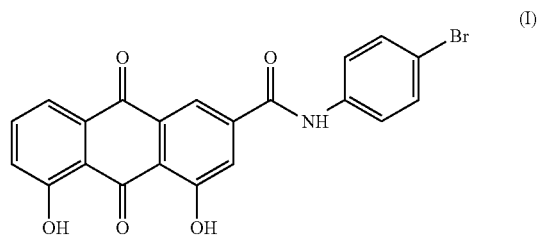 [SMILES: O=C(Nc1ccc(Br)cc1)c1cc(O)c2c(c1)C(=O)c1cccc(O)c1C2=O]

In another embodiment, the present invention provides two methods of preparing the compound of formula (I). The first method involves reacting the compound of formula (II) with the compound of formula (III) in organic solvent to obtain the compound of formula (I):

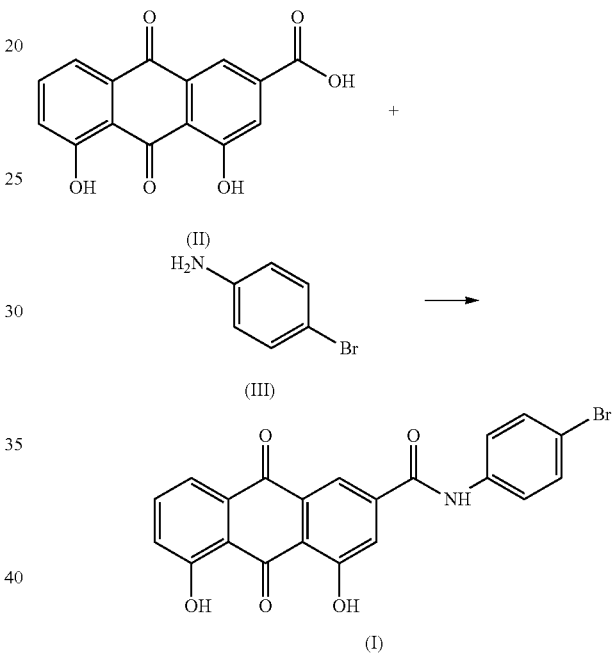

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of EDC to obtain a reaction mixture; and heating the reaction mixture at 60-90° C. for 3-7 hours; and purifying the crude product on a silica gel fresh chromatography column with petroleum ether and ethyl acetate as an eluent to obtain the compound of formula (I).

In another embodiment, the organic solvent is toluene, tetrahydrofuran or acetonitrile.

In another embodiment, the organic solvent is toluene.

In another embodiment, the molar ratio of the compound of formula (II) and the compound of formula (III) is 1:1.1.

In another embodiment, the reaction mixture is heated at 80° C.

In another embodiment, the reaction mixture is heated for 5 hours.

In another embodiment, the eluent is petroleum ether: ethyl acetate=1:3.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 30-60° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-butyl-3-methylimidazolium tetrafluoroborate ([BMIM][$BF_4$]).

In another embodiment, the molar ratio of the compound of formula (II) and the compound of formula (III) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
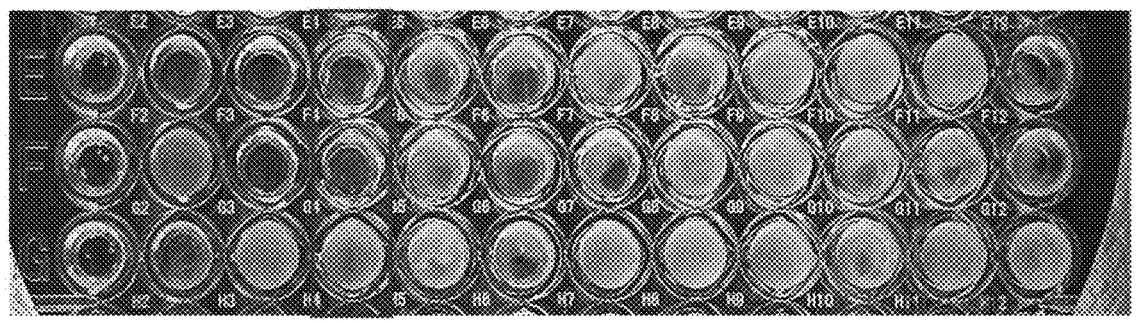
FIG. 1 shows the results of in vitro antibacterial activity of p-bromoaniline cassic acid ester against drug-resistant bacteria MDR-PA 18-174.

Reference will now be made in detail to embodiments of the present invention, example of which is illustrated in the accompanying drawings. The following examples illustrate the present invention, but the present invention is not limited to the following examples.

Example 1

Preparation of N-(4-bromophenyl)-4,5-dihydroxy-9,10-dioxo-9,10-dihydroanthracene-2-carboxamide (Compound of formula I)

In a 250 mL three-necked flask, 200.0 mg (0.7 mmol) of cassic acid and 134.0 mg (0.7 mmol) EDC (1-ethyl-3-(3-dimethylaminopropyl)carbodiimide) were dissolved in 100 mL of toluene under nitrogen atmosphere. 131.6 mg (0.77 mmol) of p-bromoaniline was dissolved in 20 mL of toluene, and slowly added dropwise to the reaction mixture by a separatory funnel. After the completion of the dropwise addition, the temperature was raised to 80° C., and the reaction was carried out for 5 hours. Thin layer chromatography was used to track the reaction to completion, heating was stopped, and the protective device was removed. The reaction mixture was concentrated under reduced pressure. The concentrated solution was washed in water, extracted with ethyl acetate, dried and concentrated to obtain a crude product. The crude product was purified by silica gel column chromatography with petroleum ether:ethyl acetate=1:3 as eluent, and the eluent was concentrated under reduced pressure and dried to obtain 223.9 mg of the title compound, a total yield of 73.21%.

$^1$H-NMR (400 MHz, DMSO-$d_6$) δ (ppm): 11.90 (1H, s), 8.16 (1H, s), 7.86 (2H, d), 7.78 (2H, d), 7.42 (3H, d), 7.13 (2H, s), 6.54 (1H, d); $^{13}$C-NMR (400 MHz, DMSO-$d_6$) δ (ppm): 191.8, 181.4, 165.8, 161.9, 148.5, 138.0, 133.6, 131.7, 124.6, 119.3, 116.3, 106.5.

Example 2

Preparation of N-(4-bromophenyl)-4,5-dihydroxy-9,10-dioxo-9,10-dihydroanthracene-2-carboxamide (Compound of formula I)

In a 250 mL three-necked flask, 200.0 mg (0.7 mmol) of cassic acid and 134.0 mg (0.7 mmol) EDC were dissolved in 100 mL of acetonitrile under nitrogen atmosphere. 131.6 mg (0.77 mmol) of p-bromoaniline was dissolved in 20 mL of acetonitrile, and slowly added dropwise to the reaction mixture by a separatory funnel. After the completion of the dropwise addition, the temperature was raised to 60° C., and the reaction was carried out for 7 hours. Thin layer chromatography was used to track the reaction to completion, heating was stopped, and the protective device was removed. The reaction mixture was concentrated under reduced pressure. The concentrated solution was washed in water, extracted with ethyl acetate, dried and concentrated to obtain a crude product. The crude product was purified by silica gel column chromatography with petroleum ether: ethyl acetate=1:3 as eluent, and the eluent was concentrated under reduced pressure and dried to obtain 192.3 mg of the title compound, a total yield of 62.85%.

Example 3

Preparation of N-(4-bromophenyl)-4,5-dihydroxy-9,10-dioxo-9,10-dihydroanthracene-2-carboxamide (Compound of formula I)

In a 250 mL three-necked flask, 200.0 mg (0.7 mmol) of cassic acid and 134.0 mg (0.7 mmol) EDC were dissolved in 100 mL of tetrahydrofuran under nitrogen atmosphere. 131.6 mg (0.77 mmol) of p-bromoaniline was dissolved in 20 mL of tetrahydrofuran, and slowly added dropwise to the reaction mixture by a separatory funnel. After the completion of the dropwise addition, the temperature was raised to 90° C., and the reaction was carried out for 3 hours. Thin layer chromatography was used to track the reaction to completion, heating was stopped, and the protective device was removed. The reaction mixture was concentrated under reduced pressure. The concentrated solution was washed in water, extracted with ethyl acetate, dried and concentrated to obtain a crude product. The crude product was purified by silica gel column chromatography with petroleum ether:ethyl acetate=1:3 as eluent, and the eluent was concentrated under reduced pressure and dried to obtain 185.9 mg of the title compound, a total yield of 60.76%.

Example 4

Preparation of N-(4-bromophenyl)-4,5-dihydroxy-9,10-dioxo-9,10-dihydroanthracene-2-carboxamide (Compound of formula I)

In a 250 mL three-necked flask, 200.0 mg (0.7 mmol) of cassic acid and 134.0 mg (0.7 mmol) EDC were dissolved in 100 mL of toluene under nitrogen atmosphere. 143.6 mg (0.84 mmol) of p-bromoaniline was dissolved in 20 mL of toluene, and slowly added dropwise to the reaction mixture by a separatory funnel. After the completion of the dropwise addition, the temperature was raised to 75° C., and the reaction was carried out for 6 hours. Thin layer chromatography was used to track the reaction to completion, heating was stopped, and the protective device was removed. The reaction mixture was concentrated under reduced pressure. The concentrated solution was washed in water, extracted with ethyl acetate, dried and concentrated to obtain a crude product. The crude product was purified by silica gel column chromatography with petroleum ether:ethyl acetate=1:3 as eluent, and the eluent was concentrated under reduced pressure and dried to obtain 200.4 mg of the title compound, a total yield of 65.52%.

Example 5

Preparation of N-(4-bromophenyl)-4,5-dihydroxy-9,10-dioxo-9,10-dihydroanthracene-2-carboxamide (compound of formula I)

In a 250 mL three-necked flask, 200.0 mg (0.7 mmol) of cassic acid and 134.0 mg (0.7 mmol) EDC were dissolved in 100 mL of acetonitrile under nitrogen atmosphere. 143.6 mg (0.84 mmol) of p-bromoaniline was dissolved in 20 mL of acetonitrile, and slowly added dropwise to the reaction mixture by a separatory funnel. After the completion of the dropwise addition, the temperature was raised to 80° C., and the reaction was carried out for 6 hours. Thin layer chromatography was used to track the reaction to completion, heating was stopped, and the protective device was removed. The reaction mixture was concentrated under reduced pressure. The concentrated solution was washed in water, extracted with ethyl acetate, dried and concentrated to obtain a crude product. The crude product was purified by silica gel column chromatography with petroleum ether:ethyl acetate=1:3 as eluent, and the eluent was concentrated under reduced pressure and dried to obtain 210.2 mg of the title compound, a total yield of 68.71%.

Example 6

Preparation of N-(4-bromophenyl)-4,5-dihydroxy-9,10-dioxo-9,10-dihydroanthracene-2-carboxamide (Compound of formula I)

In a 250 mL three-necked flask, 200.0 mg (0.7 mmol) of cassic acid and 134.0 mg (0.7 mmol) EDC were dissolved in 100 mL of tetrahydrofuran under nitrogen atmosphere. 131.6 mg (0.77 mmol) of p-bromoaniline was dissolved in 20 mL of tetrahydrofuran, and slowly added dropwise to the reaction mixture by a separatory funnel. After the completion of the dropwise addition, the temperature was raised to 70° C., and the reaction was carried out for 5 hours. Thin layer chromatography was used to track the reaction to completion, heating was stopped, and the protective device was removed. The reaction mixture was concentrated under reduced pressure. The concentrated solution was washed in water, extracted with ethyl acetate, dried and concentrated to obtain a crude product. The crude product was purified by silica gel column chromatography with petroleum ether:ethyl acetate=1:3 as eluent, and the eluent was concentrated under reduced pressure and dried to obtain 197.9 mg of the title compound, a total yield of 64.69%.

Example 7

Preparation of N-(4-bromophenyl)-4,5-dihydroxy-9,10-dioxo-9,10-dihydroanthracene-2-carboxamide (Compound of formula I)

In a 250 mL three-necked flask, 200.0 mg (0.7 mmol) of cassic acid, 131.6 mg (0.77 mmol) of p-bromoaniline and 12.0 mg (0.007 mmol) silicomolybdic acid were dissolved in 100 mL of 1-butyl-3-methylimidazolium tetrafluoroborate under nitrogen atmosphere. After full dissolution, the temperature of the reaction mixture was raised to 30° C. and the reaction was carried out for 6 hours. Thin layer chromatography was used to track the reaction to completion, heating was stopped, and the protective device was removed. The reaction mixture was allowed to separate into layers to give a crude product. The crude product was recrystallized in 50 mL methanol to 257.4 mg of the title compound, a total yield of 84.15%.

Example 8

Preparation of N-(4-bromophenyl)-4,5-dihydroxy-9,10-dioxo-9,10-dihydroanthracene-2-carboxamide (Compound of formula I)

In a 250 mL three-necked flask, 200.0 mg (0.7 mmol) of cassic acid, 131.6 mg (0.77 mmol) of p-bromoaniline and 12.0 mg (0.007 mmol) silicomolybdic acid were dissolved in 100 mL of 1-butyl-3-methylimidazolium tetrafluoroborate under nitrogen atmosphere. After full dissolution, the temperature of the reaction mixture was raised to 60° C. and the reaction was carried out for 4 hours. Thin layer chromatography was used to track the reaction to completion, heating was stopped, and the protective device was removed. The reaction mixture was allowed to separate into layers to give a crude product. The crude product was recrystallized in 50 mL methanol to 234.7 mg of the title compound, a total yield of 76.73%.

Example 9

Antibacterial Activity Test

The minimal inhibitory concentration (MIC) of the compounds as determined by microbroth dilution method with gentamicin, cefazolin sodium and ceftriaxone sodium as positive control.

The experimental strains included methicillin-resistant Gram-positive bacteria: methicillin-resistant *Staphylococcus aureus* MRSA 18-222, 18-575; multiple drug-resistant Gram-negative bacteria: vancomycin-resistant *enterococci* VRE 18-80, 18-94, multidrug-resistant *Pseudomonas aeruginosa* MDR-PA 18-1774, 18-202, carbapenem-resistant *Acinetobacter baumannii* CR-AB 18-183, 18-560. All the experimental strains were donated by Huashan Hospital affiliated to Fudan University (Institute of Antibiotics, Fudan University) and used after routine identification.

Preparation of Test Strains:

Preparation of MHB medium: 20.0 g MHB medium was added to 1 L distilled water, boiled until completely dissolved, packed in conical bottles and sterilized at 121° C. for 15 min.

The experimental strain was cultured to the logarithmic growth phase: under aseptic condition, the experimental strain was inoculated into 100 mL MHB medium and incubated in a constant temperature and humidity incubator at 37° C. for 20-22 hours.

Preparation of storage solution: weighing the sample to be tested, dissolving it with 1% DMSO solution, preparing a storage solution with a concentration of 2560 μg/mL; weighing a positive reference substance, dissolving it with aseptic distilled water, and configuring a storage solution with a concentration of 2560 μg/mL.

Preparation of bacterial suspension: under aseptic condition, the experimental strains cultured to logarithmic growth phase were adjusted to 0.5 MCF turbidity standard with MHB medium and diluted according to 1:10, and the bacterial suspension with concentration of $10^6$ CFU/mL was prepared for standby.

Dilution of storage solution and inoculation of experimental strain: under aseptic condition, the storage solution was diluted to 256 μg/mL solution; taking a sterile 96-well plate, adding 200 μL MHB medium to the 12th well, and adding 100 μL MHB medium to each well; adding 100 μL of positive control solution to the first well, mixing well, and sucking 100 μL from it and discarding; adding 100 μL of the compound sample solution to the second well, mixing well, and then pipetting 100 μL to the third well; after mixing, pipetting 100 μL to the fourth well, and diluting to the 11th well in this way; finally, 100 μL was pipetted from the 11th well and discarded, the 12th hole was the growth control without drugs. The concentration of the positive reference substance is 128 μg/mL; the concentrations of the sample solution are 128, 64, 16, 8, 4, 2, 1, 0.5, 0.25 μg/mL, respectively. Then, 100 μL of the prepared bacterial suspension is added to each well, so that the final concentration of the bacterial liquid in each well is $5 \times 10^5$ CFU/mL.

Incubation: covering the 96-well plate inoculated with the experimental strains, and incubating in a constant temperature and humidity box at 37° C. for 20-22 hours.

Interpretation of the MIC endpoint: the concentration that can completely inhibit the growth of bacteria in a 96-well plate under a black background is the lowest inhibitory concentration of the sample against the bacteria.

In FIGS. 1-6, the twelve wells represent twelve groups, from left to right, positive, 128 μg/mL, 64 μg/mL, 32 μg/mL, 16 μg/mL, 8 μg/mL, 4 μg/mL, 2 μg/mL, 1 μg/mL, 0.25 μg/mL, 0.0625 μg/mL, Negative.

Figure 2:
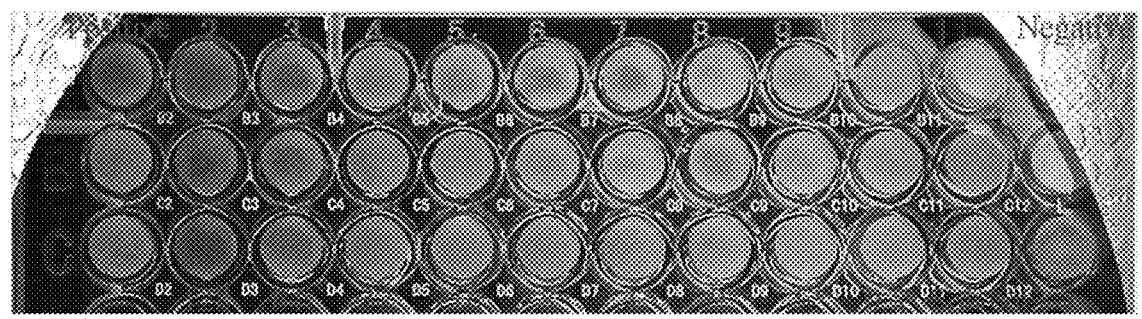
FIG. 2 shows the results of in vitro antibacterial activity of cassic acid against drug-resistant bacteria MDR-PA 18-174.
Figure 3:
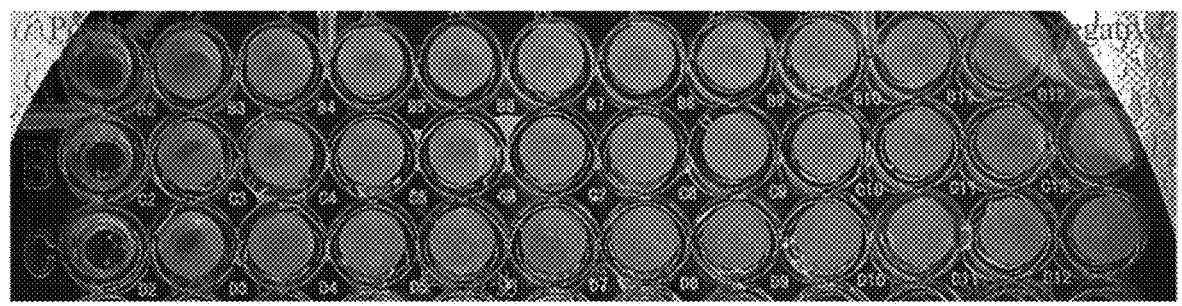
FIG. 3 shows the results of in vitro antibacterial activity of p-bromoaniline against drug-resistant bacteria MDR-PA 18-174.
Figure 4:
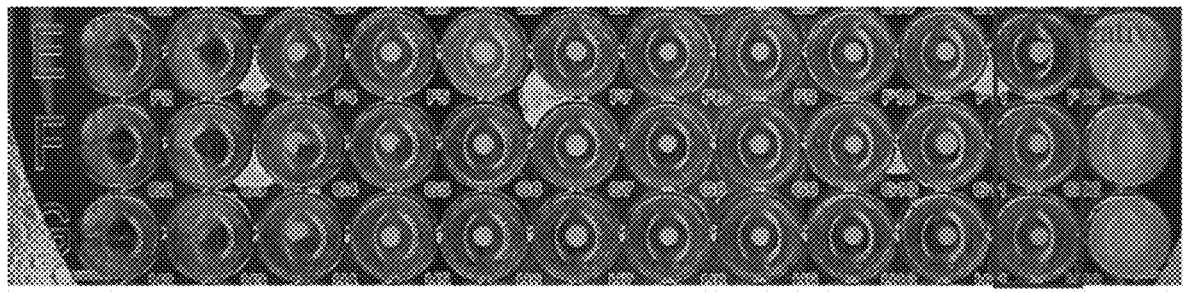
FIG. 4 shows the results of in vitro antibacterial activity of gentamicin against drug-resistant bacteria MDR-PA 18-174.
Figure 5:
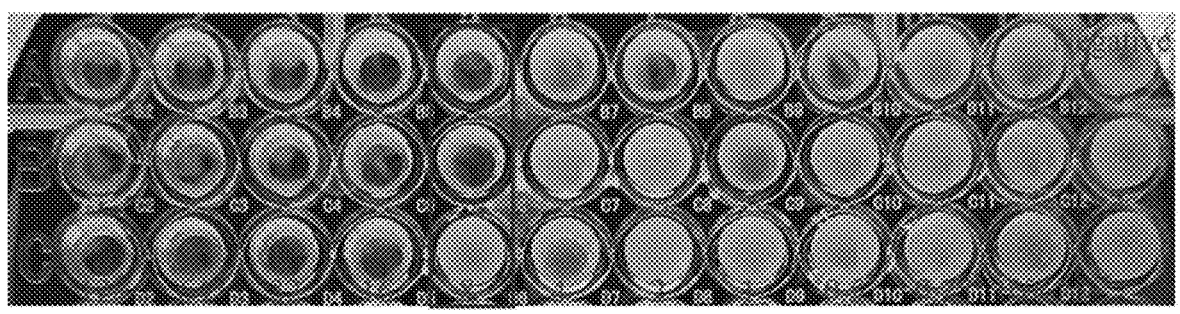
FIG. 5 shows the results of in vitro antibacterial activity of cefazolin sodium against drug-resistant bacteria MDR-PA 18-174.
Figure 6:
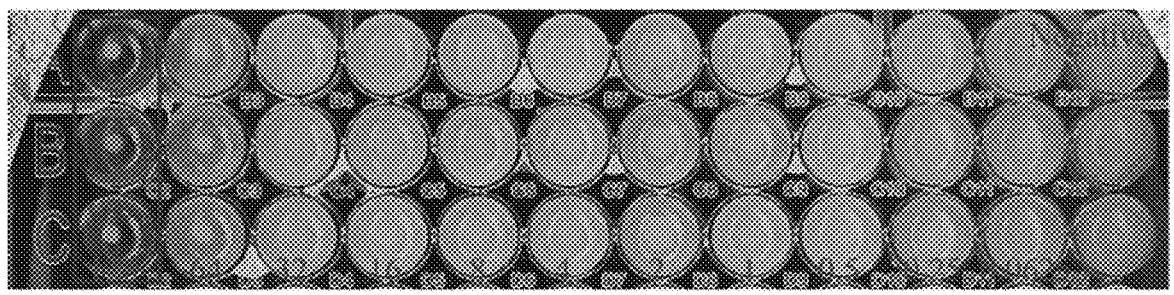
FIG. 6 shows the results of in vitro antibacterial activity of ceftriaxone sodium against drug-resistant bacteria MDR-PA 18-174.

FIG. 1 shows the in vitro antibacterial activity of p-bromoaniline cassic acid ester (compound of formula I) against drug-resistant bacteria MDR-PA 18-174. FIG. 2 shows the in vitro antibacterial activity of cassic acid against drug-resistant bacteria MDR-PA 18-174. FIG. 3 shows the in vitro antibacterial activity of p-bromoaniline against drug-resistant bacteria MDR-PA 18-174. FIG. 4 shows the in vitro antibacterial activity of gentamicin against drug-resistant bacteria MDR-PA 18-174. FIG. 5 shows the in vitro antibacterial activity of cefazolin sodium against drug-resistant bacteria MDR-PA 18-174. FIG. 6 shows the in vitro antibacterial activity of ceftriaxone sodium against drug-resistant bacteria MDR-PA 18-174. The results are summaried in Table 1.

TABLE 1

Minimum bacteriostatic concentration of test drug and positive drug ($\mu g \cdot mL^{-1}$)

| | Strain | | | | | | | |
|---|---|---|---|---|---|---|---|---|
| | MRSA | | VRE | | MDR-PA | | CR-AB | |
| Sample | 18-222 | 18-575 | 18-80 | 18-94 | 18-174 | 18-202 | 18-183 | 18-560 |
| p-Bromoaniline cassic acid ester | >128 | >128 | >128 | 128 | 32 | >128 | >128 | >128 |
| Gentamicin | 128 | 2 | 0.0625 | >128 | 0.0625 | 0.0625 | >128 | >128 |
| Cefazolin sodium | >128 | >128 | 32 | >128 | 8 | 128 | >128 | >128 |
| Ceftriaxone sodium | >128 | >128 | 8 | >128 | 128 | 16 | >128 | >128 |
| Cassic acid | >128 | >128 | >128 | >128 | >128 | >128 | >128 | >128 |
| P-Bromoaniline | >128 | >128 | >128 | >128 | >128 | >128 | >128 | >128 |

The experimental results show that cassic acid and p-bromoaniline have no inhibitory effect on drug-resistant bacteria. p-Bromoaniline cassic acid ester shows a strong inhibitory effect on multi-drug resistant *Pseudomonas aeruginosa* MDR-PA (MIC=32 μg/mL) as well as vancomycin-resistant *enterococci* VRE 18-94 (MIC=128 μg/mL). In summary, p-bromoaniline cassic acid ester of the present invention can be used as an antibacterial drug candidate for multi-drug resistant *Pseudomonas aeruginosa* of gram-negative bacteria, and further pre-clinical research.

What is claimed is:

1. A compound of the following formula (I):

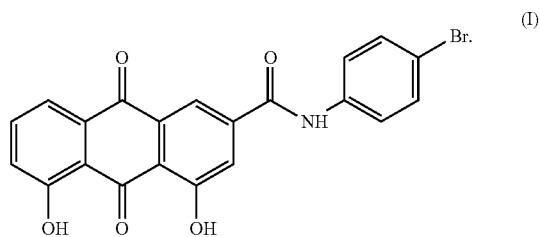 [SMILES: O=C(Nc1ccc(Br)cc1)c1cc(O)c2c(c1)C(=O)c1cccc(O)c1C2=O]

2. A method of preparing the compound of formula (I) of claim 1, comprising: reacting the compound of formula (II) with the compound of formula (III) to obtain the compound of formula (I):

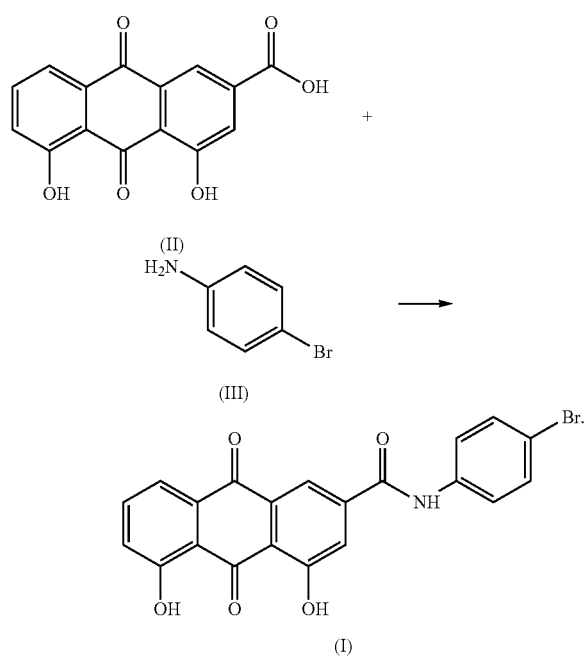

3. The method of claim 2, wherein the reaction of the compound of formula (II) with the compound of formula (III) comprises the following steps:
  placing the compound of formula (II) and the compound of formula (III), in a molar ratio of 1:1 to 1:1.3, in a reactor;
  adding an organic solvent and a catalytic amount of EDC under nitrogen atmosphere to obtain a reaction mixture; and
  heating the reaction mixture at 60-90° C. for 3-7 hours; and
  purifying the crude product on a silica gel fresh chromatography column with petroleum ether and ethyl acetate as an eluent to obtain the compound of formula (I).

4. The method of claim 3, wherein the organic solvent is toluene, tetrahydrofuran or acetonitrile.

5. The method of claim 4, wherein the organic solvent is toluene.

6. The method of claim 3, wherein the molar ratio of the compound of formula (II) and the compound of formula (III) is 1:1.1.

7. The method of claim 3, wherein the reaction mixture is heated at 80° C.

8. The method of claim 3, wherein the reaction mixture is heated for 5 hours.

9. The method of claim 3, wherein the eluent is petroleum ether:ethyl acetate=1:3.

10. The method of claim 2, wherein the reaction of the compound of formula (II) with the compound of formula (III) comprises the following steps:
  placing the compound of formula (II), a catalyst, and an ionic liquid in a reactor under nitrogen atmosphere, the catalyst being 12-molybdosilicic acid hydrate ($H_6Mo_{12}O_{41}Si$);
  adding the compound of formula (III) to the reactor to form a reaction mixture;
  heating the reaction mixture at 30-60° C. for 4-8 hours;
  placing the reaction mixture in a separating funnel to separate a crude product;
  purifying the crude product by recrystallization in methanol to obtain the compound of formula (I); and
  recycling the ionic liquid.

11. The method of claim 10, wherein the ionic liquid is 1-butyl-3-methylimidazolium tetrafluoroborate ([BMIM][$BF_4$]).

12. The method of claim 10, wherein the compound of formula (II) and the compound (III) have a molar ratio of 1:1 to 1:1.3.

13. The method of claim 12, wherein the molar ratio of the compound of formula (II) and the compound of formula (III) is 1:1.1.

14. The method of claim 10, wherein the reaction mixture is heated at 30° C.

15. The method of claim 10, wherein the reaction mixture is heated for 6 hours.

* * * * *